US005312353A

United States Patent [19]

Boggess et al.

[11] Patent Number: 5,312,353

[45] Date of Patent: May 17, 1994

[54] MODULAR POULTRY AUTOMATIC VACCINE INJECTION AND SPRAY APPARATUS

[76] Inventors: Gregory D. Boggess, 3812 Woodlane Cir., Gainesville, Ga. 30506; Joseph H. Johnson, Gainesville, Ga.; Richard M. Kight, Stone Mountain, Ga.; John D. Mason, Decatur, Ga.; Roger D. Luke, Stone Mountain, Ga.

[21] Appl. No.: 36,462

[22] Filed: Mar. 24, 1993

[51] Int. Cl.[5] .......................... A61M 5/20; A61D 7/00

[52] U.S. Cl. ...................................... 604/144; 604/156

[58] Field of Search ............... 604/144, 156, 143, 147, 604/131

[56] References Cited

U.S. PATENT DOCUMENTS

| | | | |
|---|---|---|---|
| 2,782,682 | 2/1957 | Browning et al. | 604/156 |
| 2,918,063 | 12/1959 | Tucker | 128/218 |
| 3,641,998 | 2/1972 | Lyon | 128/218 |
| 3,675,651 | 7/1972 | Meyer | 128/218 |
| 3,777,752 | 12/1973 | Goodwin | 128/173 |
| 3,964,481 | 6/1976 | Gourlandt | 128/218 |
| 4,108,176 | 8/1978 | Walden | 128/218 |
| 4,177,810 | 12/1979 | Gourlandt | 128/218 |
| 4,276,879 | 7/1981 | Yiournas | 128/218 |
| 4,449,968 | 5/1984 | Peterson | 604/24 |
| 4,515,590 | 5/1985 | Daniel | 604/144 |
| 4,681,565 | 7/1987 | Gourlandt | 604/156 |
| 4,758,227 | 7/1988 | Lancaster, Jr. et al. | 604/156 |
| 4,863,443 | 9/1989 | Hornung | 604/141 |
| 5,024,664 | 6/1991 | Mitchell | 604/131 |

FOREIGN PATENT DOCUMENTS 1452790 10/1973 United Kingdom .

*Primary Examiner*—Paul J. Hirsch

[57] ABSTRACT

A modular poultry automatic injection and spraying apparatus (10) featuring a dual-sensor switch means (41) and a dual-action, fluid-actuated drive means (101) is disclosed. The apparatus has a casing construction (11) including an upper housing (12) mounted on a lower housing (13) such that the lower housing (13), which contains water-sensitive pneumatic logic circuitry (261), can be easily removed prior to cleaning. The casing construction (11) has the additional advantage of allowing substitute upper and lower housings (12, 13) to be interchanged during maintenance and repair. The dual sensor switch means (41) ensures that the injections are performed accurately and consistently. The dual-action, fluid-actuated drive means (101) allows for the simultaneous injection and spraying functions of the apparatus (10) obviating the need for an additional apparatus or separate compressed air signal. The apparatus (10) also features a compressed air flushing system which prevents the switch means (41) from clogging, and periodically flushes contaminants from the lower housing (13), using exhaust from an alarm means (71), which notifies an operator of a complete run. Additionally, a separation means (21) prevents chicks, y missed by the apparatus (10) due to operator error, from mixing with chicks already inoculated by the apparatus (10).

30 Claims, 8 Drawing Sheets

MODULAR POULTRY AUTOMATIC VACCINE INJECTION AND SPRAY APPARATUS

FIELD OF THE INVENTION

The subject invention relates to a device for injecting and/or spraying baby chickens and other small fowl and small animals with a vaccine. More particularly the invention comprises a modular vaccine injector and spray apparatus which provides improved chick handling and reliable inoculation of the chicks for use in commercial hatcheries.

BACKGROUND OF THE INVENTION

The process of inoculating one day old chicks and other fowl has become fairly commonplace in the commercial hatchery industry. One person with an automated vaccinator can inoculate thousands of chicks per day. Such devices are described in, U.S. Pat. Nos. 4,863,443 to Hornung, 4,515,590 to Daniel, 4,177,810 to Gourlandt and 4,108,176 to Walden.

The inoculation process involves placing one chick at a time on a known injection device, which detects the chick and cycles through its injection procedures. The chick, presumably inoculated, is then released by the operator, slides off the injection device and falls into a container for the inoculated chicks. This procedure is repeated for a preselected number of chicks, usually a run of one hundred, at which point the injection device notifies the operator with a sound alarm. The operator then replaces the now-filled container of inoculated chicks with an empty container and begins a new run.

The prior art inoculation devices usually comprise a single, outer housing within which is contained all necessary mechanical and electrical components of the inoculation system. The housing usually includes an inclined work surface on which the chick to be injected is placed, the surface having an aperture through which a syringe needle reciprocrates to inject the chick, a syringe mounted on the opposite side of the work plane for urging vaccine through the needle when the needle penetrates the chick and a switch and switch housing mounted on the work surface adjacent the aperture.

However, the known devices are not entirely satisfactory. With the prior art chick switch housings it is difficult to ensure that each chick is aligned correctly with regard to the syringe needle when the operators use their fast hand movements during the inoculation procedures. An improperly located injection can result in an inadequate inoculation, injury or even death to the chick. In addition, due to the repetition and haste with which the operator handles the chicks, it is common for chicks to be placed near the switch housing without actuating the switch and without causing the system to cycle. Thus, an undesirable percentage of uninoculated chicks are mixed in the container with inoculated chicks.

In addition, because the environment in commercial hatcheries is far from clean and because of the repetitive contact between the chicks and the switch, it is common for the switch housing to become clogged with feathers, etc. It then becomes necessary to halt the inoculation process in order to clean or replace the switch, thus resulting in down time and fewer inoculated chicks per day.

The outer housing of the prior art inoculators also requires frequent cleaning; however, a quick, liquid washdown is not possible because of the proximity of water-sensitive components contained within the housing.

It is also common for the compartment within the housing to become contaminated with feathers, dirt and other matter. In order to clean the compartment, it is sometimes necessary to remove from the housing some of the working components of the system and clean the compartment by hand or with a compressed air blower, resulting in further down time and less productivity.

The productivity of each operator is further reduced because of the number of hours the operator must spend at the end of each day cleaning and sterilizing the syringe and supply conduits contaminated by the vaccine.

With the known injection devices, an additional spray apparatus can be separately attached to the injection device for spraying vaccine to the eyes of the chicks as the chicks are inoculated. The known spray attachments require a separate compressed air signal in order to drive the topical spray.

SUMMARY OF THE INVENTION

Briefly described, the present invention comprises a device for injecting and/or spraying a baby chick or other baby fowl or animal with a desired vaccine or other fluid substance. The device comprises an upper housing adapted to mount on and plug into a lower housing. The upper housing includes a sloped work surface on which the chick to be vaccinated is placed, a hypodermic needle aperture located in the work surface, first and second disposable syringes, a hypodermic needle in fluid communication with the first syringe, a spray apparatus mounted on the upper housing and in fluid communication with the second syringe, and drive means for moving the needle from within the housing through the aperture to penetrate chicks outside the housing and for injecting vaccine from the first syringe through the needle into the chicks and for spraying vaccine from the second syringe through the spray apparatus onto the chicks. The upper housing also includes switch means mounted on the sloped work surface responsive to the presence of a chick for actuating the drive means. The lower housing contains most of the pneumatic logic circuitry necessary for controlling the drive means.

The switch means mounted on the housing comprises a switch housing and first and second movable switch actuator means. The switch housing includes first and second abutment surfaces facing the hypodermic needle aperture and located at different positions about the aperture. The switch housing further includes a chick retention means formed in a shape which corresponds to the shape of the head and upper back portion of a typical chick for guiding the chick to a position aligned with the aperture and with the switch means during vaccination.

The first and second movable switch actuator means are mounted in the switch housing and protrude from the abutment surfaces. The switch means further comprises a compressed air source, the first and second abutment surfaces each define an outlet opening in communication with the compressed air source and through which compressed air flows, the first and second switch actuator means each having a plug mounted for movement toward and away from the outlet opening between an open position wherein compressed air flows freely through the outlet opening and about the plug and a closed position wherein the compressed air is blocked from escaping the outlet opening and about the plug, and sensing means for detecting stoppage of compressed air flow through both outlet openings and for actuating the drive means.

The switch means is adapted to activate the drive means when both first and second switch actuator means are simultaneously moved by a chick which has been placed by an operator into engagement with both abutment surfaces, whereby when both movable switch actuator means are simultaneously moved by the chick the drive means is activated and the chick is inoculated. The use of compressed air through the switch actuator means has the further advantage of preventing the switch actuator means from becoming clogged by feathers, dirt and the like during operation of the apparatus. A compressed air signal is also used to notify the operator upon completion of a predetermined number of inoculation cycles of the apparatus. The exhaust from this compressed air signal is advantageously used to flush the housing of feathers, dirt and the like.

The drive means comprises a fluid driven cylinder/piston assembly with a cylinder movably mounted in the upper housing and a piston movably mounted in the cylinder. The hypodermic needle is responsive to the extending movement of the piston to extend through the aperture of the housing, and both the first and second syringes are responsive to the extending movement of the cylinder to contract and dispense vaccine to the needle and to the spray apparatus. When the piston and cylinder retract, the needle withdraws back through the aperture of the housing and the syringes are expanded to charge the syringes with more vaccine from external vaccine supplies.

The apparatus also comprises separation means for separating inoculated chicks from chicks placed on the housing but not inoculated. The separation means comprises a deflector plate pivotally mounted below the sloped work surface, and a fluid driven cylinder/piston assembly mounted in the lower housing. The piston of the cylinder/piston assembly is actuated in response to the closing of the switch means and the deflector plate is responsive to the movement of the piston, so that when the automatic injection apparatus cycles, the chick is inoculated, slides down the sloped work surface, is deflected by the deflector plate and falls into a container for inoculated chicks. If the chick is not properly presented to the switch means, the system does not cycle and when the chick is released by the operator the chick falls to another container for chicks that were not inoculated.

With the present invention, the number of chicks processed per hour is limited only by the operator's hand speed. Furthermore, an inoculation success rate of at least 95% is achievable due to the combination of the switch means and the separation means.

Thus, a principle object of this invention is to provide a means for accurately detecting the presence of a chick at an automatic chick inoculator so as to assure that each chick presented to the inoculator is properly inoculated.

A further object of this invention is to provide an automatic chick vaccine injection system which ensures that vaccine is delivered consistently to a predetermined location on the body of the chick with less risk of injury to the chick.

An additional object of this invention is to provide an automatic chick vaccine injection system which includes a switch means that remains unclogged and requires a chick to be properly positioned before the injection system cycles.

An additional object of this invention is to provide an automatic chick vaccine injection system which is capable of administering variable vaccine dosage amounts, while, at the same time, uses standard-sized disposable syringes.

A further object of this invention is to provide an automatic chick vaccine injection system which provides for quick and easy replacement of the syringes, needle and conduit at the end of each work day, reducing the need for time-consuming and costly sterilization procedures.

Another object of this invention is to simplify the designs of a subcutaneous injector and a topical sprayer such that both are controlled by a single drive system.

Another object of this invention is to provide an automatic chick vaccine injection system with interchangeable mechanical and interchangeable control sections for easier maintenance and less down time during repair.

Another object of this invention is to provide an automatic chick vaccine injection system which allows for easy cleanup of the housing without subjecting water-sensitive components to a liquid washdown.

A further object of this invention is to provide an automatic chick vaccine injection system which ensures that a chick released without being inoculated is separated from the desired group of inoculated chicks.

Another object of this invention is to provide an automatic chick vaccine injector system which includes an air operated alarm which indicates the end of a run and which flushes the housing compartment of contaminants using exhaust from the alarm.

Other objects, features and advantages of the present invention will become apparent upon reading the following specification, when taken in conjunction with the accompanying drawings.

BRIEF DESCRIPTION OF THE DRAWINGS

The present invention, as defined in the claims, can be better understood with reference to the following drawings. The drawings are not necessarily to scale, emphasis instead being placed upon clearly illustrating principles of the present invention.

DETAILED DESCRIPTION OF THE PREFERRED EMBODIMENT

Figure 1:
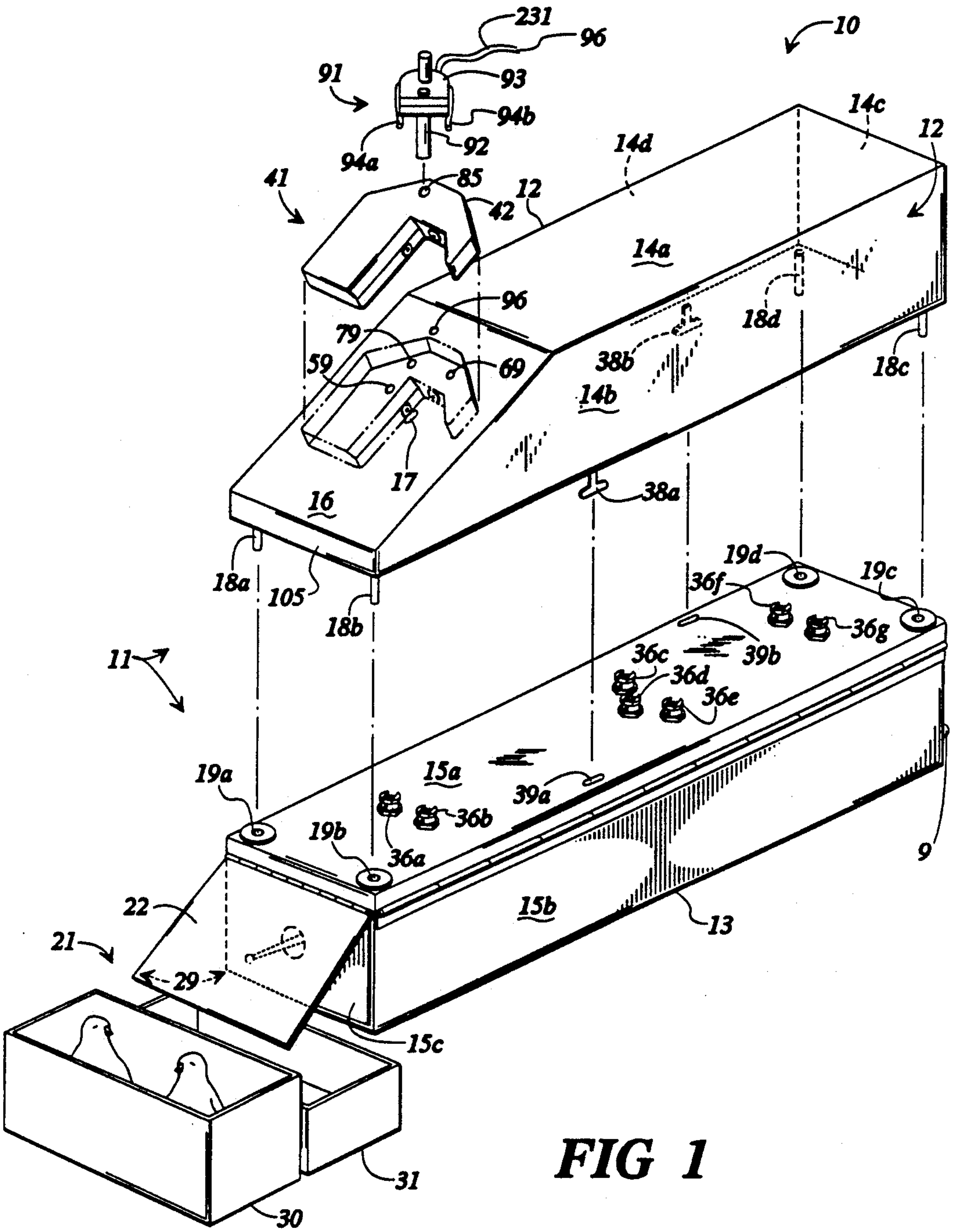
FIG. 1 is a perspective expanded view of a preferred embodiment of the automatic poultry vaccine injection and spray apparatus showing the modular casing construction and including the switch means, the spray apparatus and the separation means.
Figure 3:
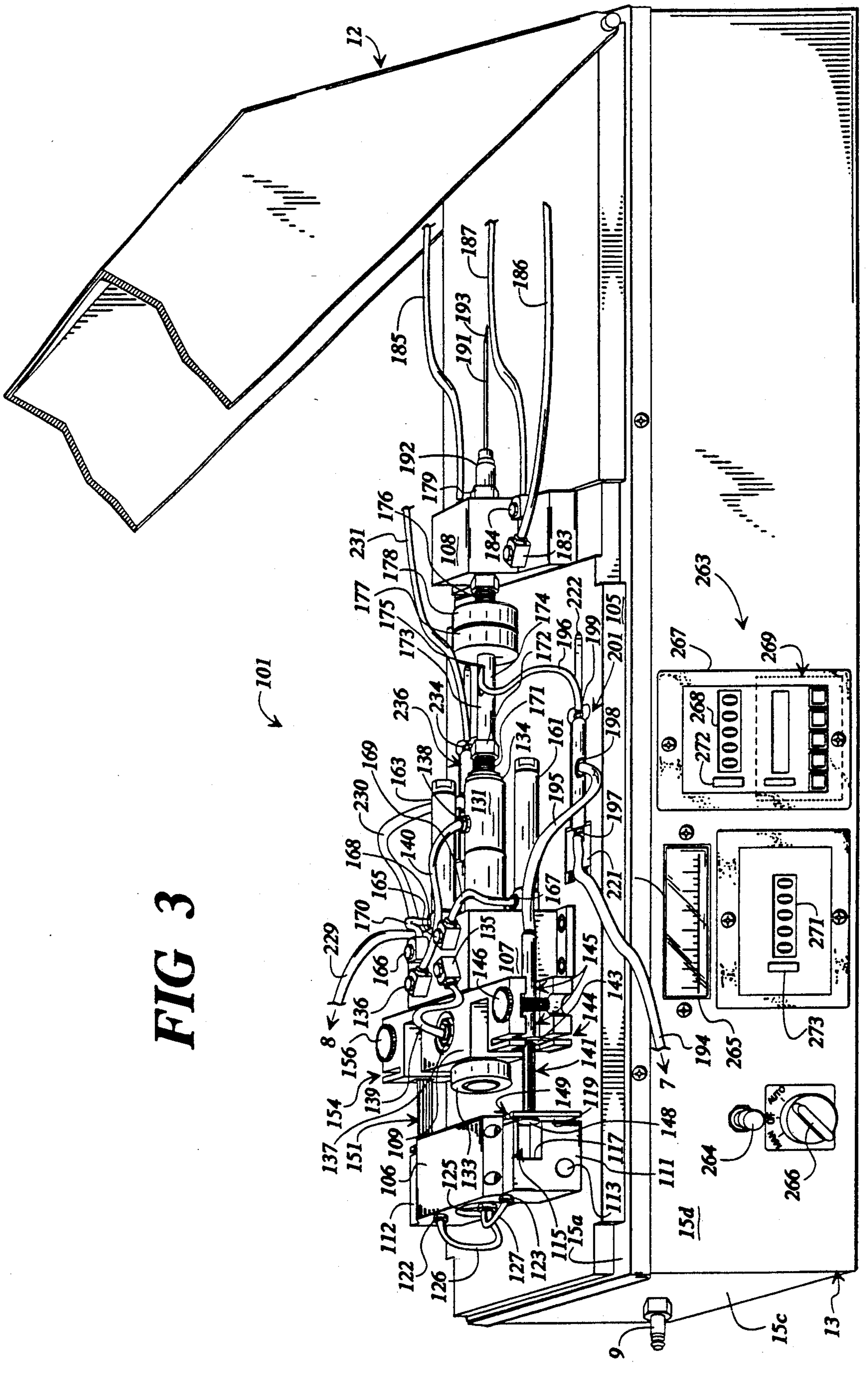
FIG. 3 is a perspective view of the pneumatically controlled drive means of the apparatus.
Figure 4:
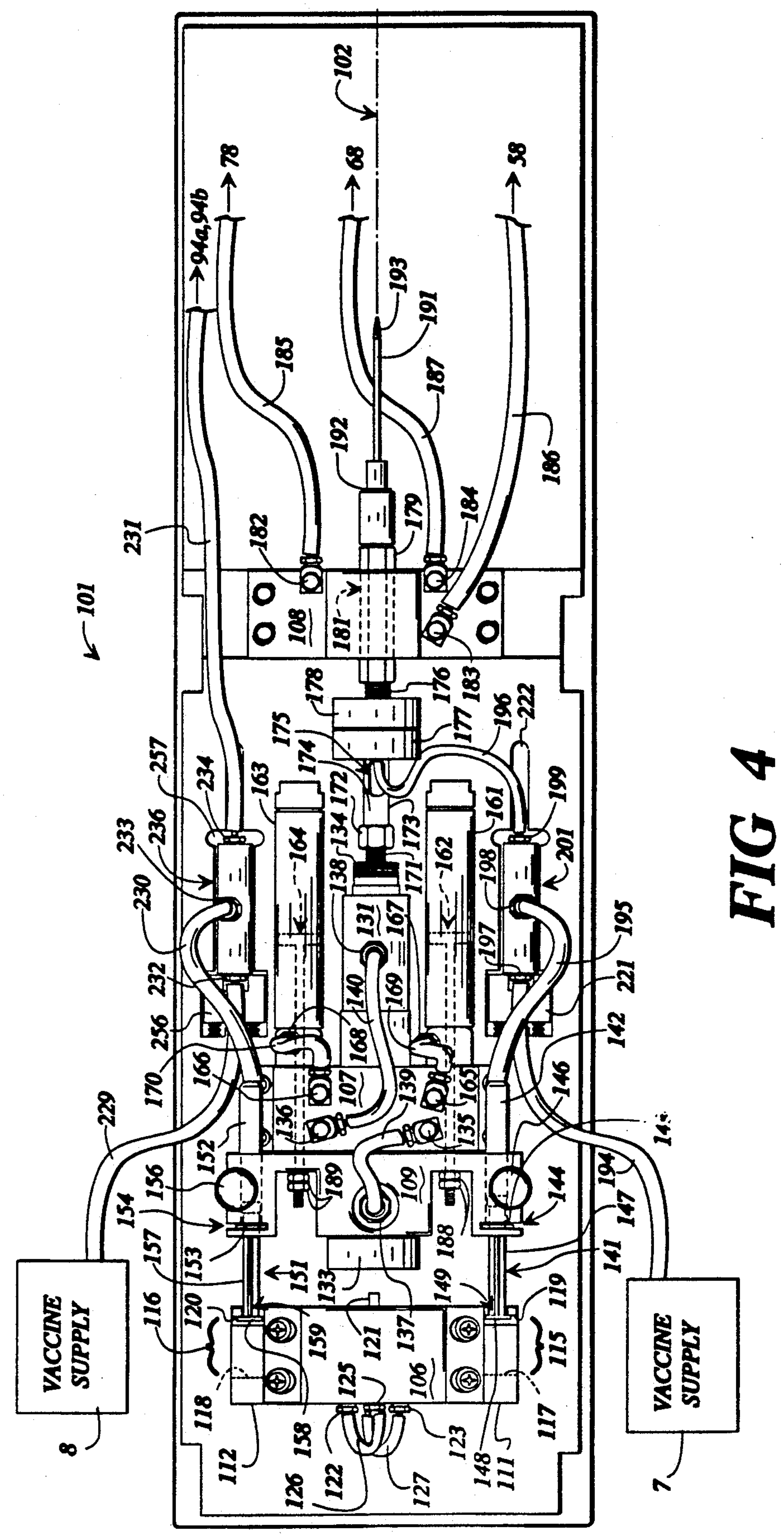
FIG. 4 is a top view of the drive means of FIG. 3.
Figure 5:
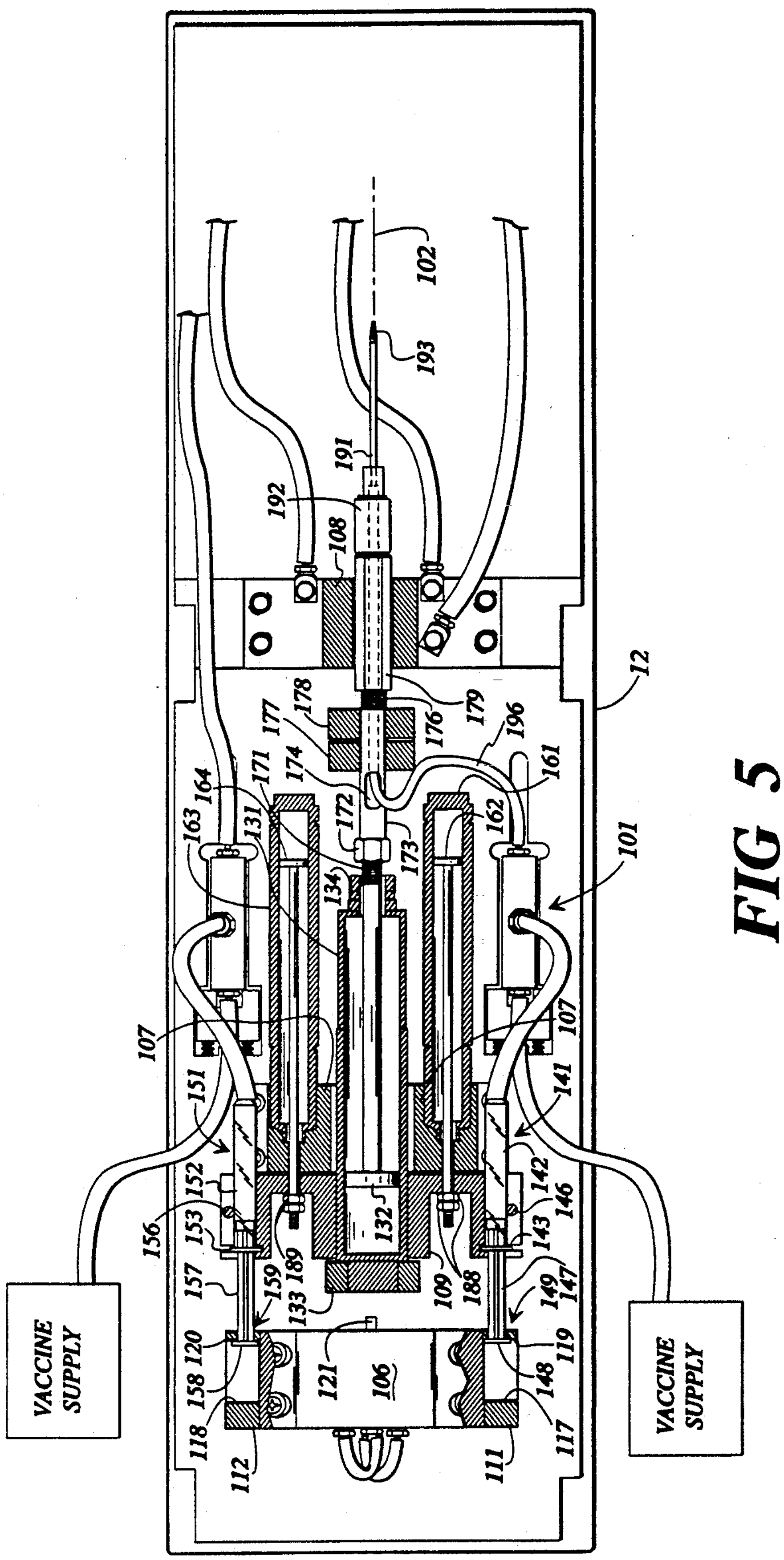
FIG. 5 is a cross-section top view of the drive means of FIGS. 3 and 4.

Referring now in more detail to the drawings, in which like numerals indicate like parts throughout the several views, FIG. 1 illustrates a front perspective view of the automatic injection spray apparatus 10. The automatic injection and spray apparatus 10 is housed in a casing construction 11 divided into an upper housing 12 and a lower housing 13. The upper housing 12 includes a plurality of side and top panels 14*a*, 14*b*, 14*c*, 14*d*, a sloped work surface 16, and a base 105. The lower housing 13 includes a plurality of side, top and bottom panels such as top, side, and front panels 15*a*, 15*b*, and 15*c*. As best shown in FIGS. 3-5, the upper housing 12 houses drive means 101, syringes 141, 151, and hypodermic needle 191. Switch means 41 (FIG. 1) and spray apparatus 91 are mounted on upper housing 12, as described in more detail below.

The lower housing 13 houses separation means 21 (FIG. 1) and most of the pneumatic logic circuitry (not shown) required to control the drive means 101. In addition, controls 263, including power switch 266, pressure gauge 265, regulator control knob 264, and counters 268, 269, 271 are mounted on side panel 15*d* of the lower housing 13 (FIG. 3).

As shown in FIG. 3, compressed air from a compressed air source (not shown) enters lower housing 13 through air supply input terminal 9. The compressed air is controlled by the pneumatic logic circuitry and moves between the lower housing 13 and the upper housing 12 through pneumatic connectors 36*a*-36*g* located on the top panel 15*a* of lower housing 13, which fit securely into mating pneumatic sockets located on the bottom side of base 105.

As illustrated in FIG. 1, the upper housing 12 is securely mounted to the lower housing 13 using alignment pins 18*a*-18*d* (FIG. 1) which are mounted to the bottom side of base 105 and are designed to fit into corresponding alignment holes 19*a*-19*d*, located on top panel 15*a* of the lower housing 13. In addition locking pins 38*a*, 38*b* and designed to fit into locking slots 39*a*, 39*b*, respectively, and can be turned a quarter-circle to lock upper housing 12 onto lower housing 13.

Switch means 41 includes switch housing 42 mounted on the sloped work surface 16 adjacent a hypodermic needle aperture 17 and on top of air supply apertures 59, 69, 79.

A spray apparatus 91 can be mounted on top of switch housing 42 by inserting mounting post 92 into mounting hole 85. Spray nozzles 94*a*, 94*b* are mounted on nozzle mount 93, which, in turn, is clamped to mounting post 92 so that during operation spray nozzles 94*a*, 94*b* are several inches above sloped work surface 16. Spray vaccine is supplied to the spray nozzles 94*a*, 94*b* through conduit 231, which extends from within upper housing 12 and through spray vaccine aperture 96. The control and flow of the spray vaccine is described in greater detail below and with reference to FIGS. 3, 4, 5, 6.

The automatic injection and spray apparatus 10 also includes separation means 21 for separating inoculated chicks from chicks placed on the sloped work surface 16 but not inoculated by the apparatus 10. The separation means 21 includes a deflector plate 22 pivotally mounted to panel 15*c* of lower housing 13. After a chick has been inoculated by apparatus 10, deflector plate 22 pivots away from lower housing 13, as shown by direction arrow 29, and the vaccinated chick, sliding down sloped work surface 16, is collected in container 30. If the apparatus 10 does not cycle, deflector plate 22 remains adjacent lower housing 13 and the unvaccinated chick slides down sloped work surface 16 and is collected in container 31 for reinoculation. The components and operation of separation means 21 are described in more detail below and with reference to FIG. 7.

FIGS. 2A, 2B, 2C and 2D illustrate various views of switch means 41. Switch means 41 comprises switch housing 42 which includes top surface 43*a*, bottom surface 43*b* (FIG. 2E) and side surfaces 43*c*-43*h*, sloped hand rest surface 44, first and second abutment surfaces 45, 46 and chick head retaining surface 48, which is part of chick retention means 47. First and second abutment surfaces 45, 46 are located substantially at right angles relative to each other and to the sloped work surface 16. Switch housing 42 is placed on sloped work surface 16 so that air supply connectors 58, 68, 78 (FIGS. 2C and 2D) protrude into upper housing 12 through air supply apertures 59, 69, 79 (FIG. 1). Switch housing 42 is firmly mounted to sloped work surface 16 by inserting screws (not shown) from the inside of upper housing 12 into threaded bores 83, 84, which protrude through bottom and top surfaces 43*b*, 43*a* of switch housing 42. First and second switch actuator means 51, 61 are correspondingly mounted in first and second abutment surfaces 45, 46

Figure 2B:
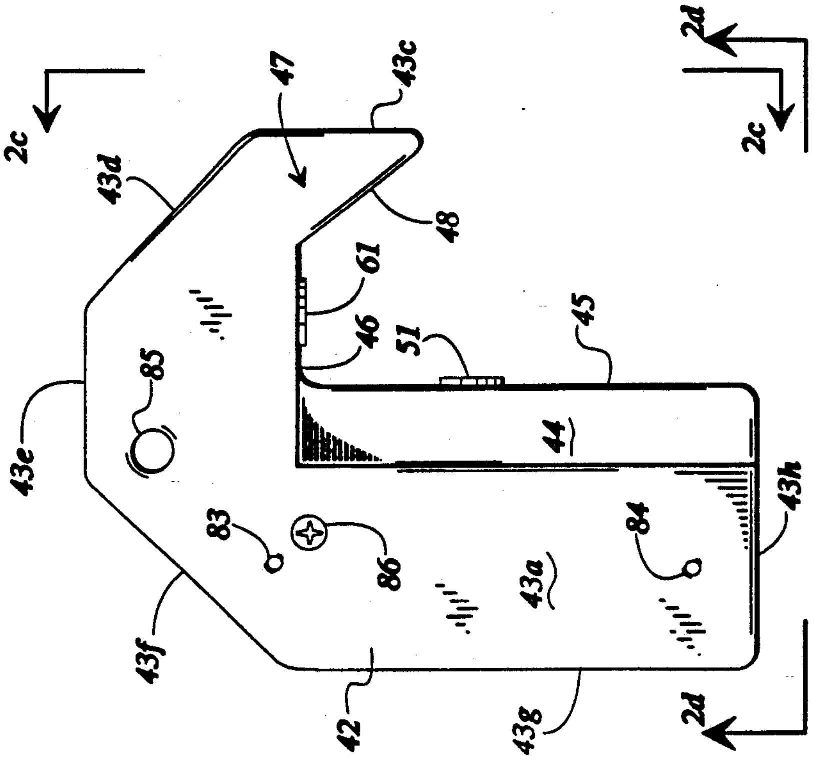
FIGS. 2B, 2C and 2D are top, front and side views of the same switch means.
Figure 2A:
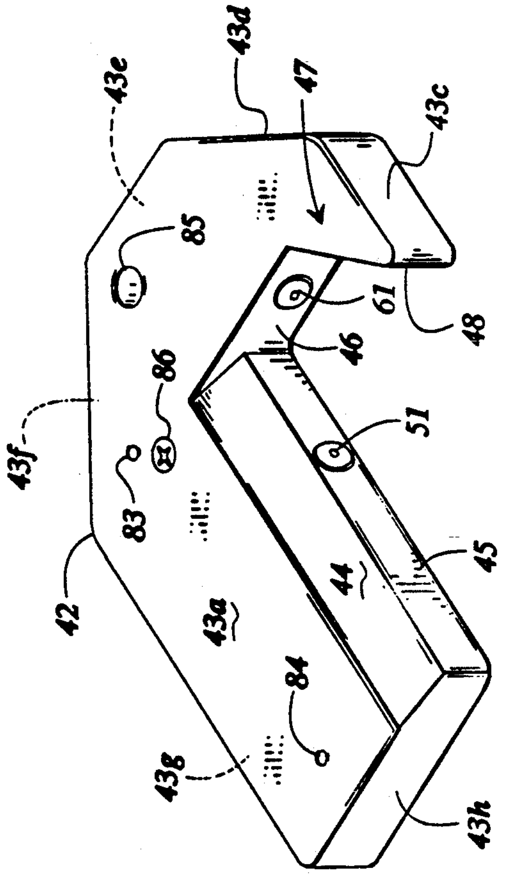
FIG. 2A illustrates an enlarged perspective view of the switch means, as shown in FIG. 1.
Figure 2E:
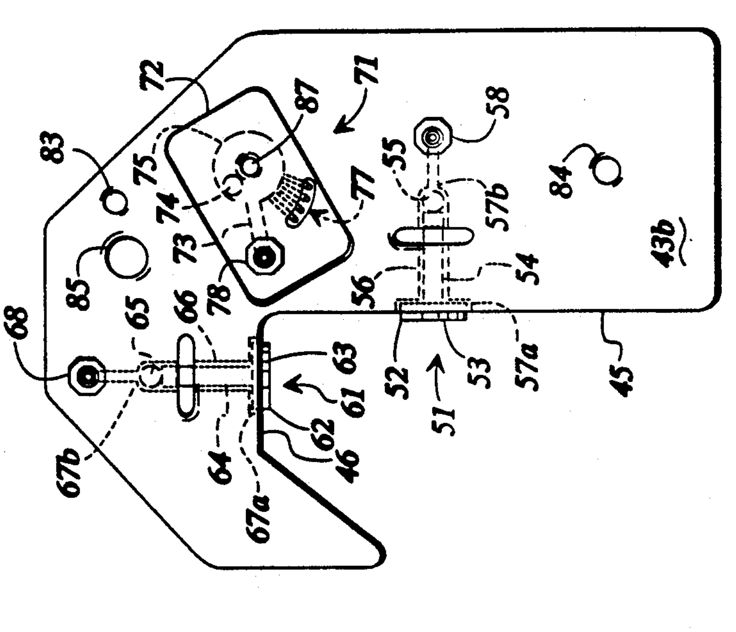
FIG. 2E is a bottom view of the same switch means, illustrating the internal components, including the alarm means, with phantom lines.
Figure 2C:
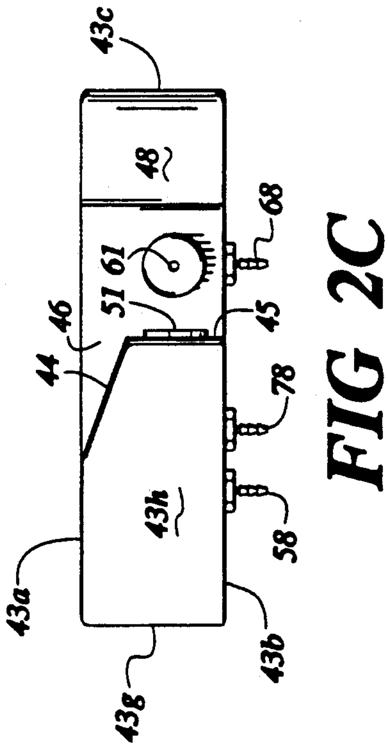
Figure 2D:
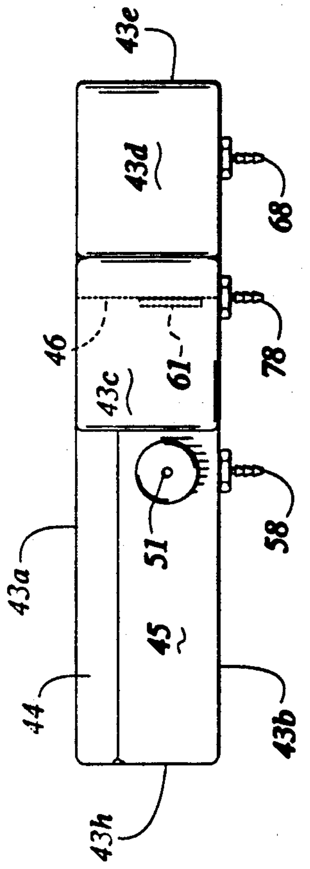

Referring now to FIG. 2E, first switch actuator means 51 comprises a plug 52, which has a plug head 53 and a plug shaft 54 movably mounted within cavity 56 and adapted to engage ball 55. Second switch actuator means 61 comprises a plug 62, which has a plug head 63 and a plug shaft 64, movably mounted within cavity 66 and adapted to engage ball 65. During operation compressed air moves from air supply connectors 58, 68 to outlet openings 57*b*, 67*b* through cavities 56, 66 and out outlet openings 57*a*, 67*a*, respectively. When plugs 52, 62 are depressed flush with abutment surfaces 45, 46, plug heads 53, 63 shut off the flow of air through outlet openings 57*a*, 67*a* and plug shafts 54, 64 engage balls 55, 65 to shut off the flow of air through outlet openings 57*b*, 67*b*, respectively. The stoppage of air through both switch actuator means 51, 61 is detected by a sensor, which, in turn, actuates drive means 101 (FIGS. 3, 4, 5) as described in more detail below.

As shown in FIG. 2E, alarm means 71 is housed in alarm housing 72. Alarm housing 72 is mounted into the bottom surface 43*b* of switch housing 42 by inserting screw 86 (FIGS. 2A and 2B) into threaded bore 87. Alarm means 71 includes a ball 74 movably mounted within circular column 75. When alarm means 71 is actuated, compressed air enters air supply connector 78 and is directed into circular column 75 by air input 73. The compressed air causes the ball 74 to travel around circular column 75, which creates a rattling noise or alarm. The air pressure in alarm housing 72 is released through exhaust ports 77 and into upper housing 12 in order to increase the pressure within the upper housing and help flush out any contaminants that might have collected in the upper housing.

FIGS. 3, 4, and 5 illustrate a perspective view, a top view and a top cross-sectional view of the pneumatically driven mechanical drive means 101 of the automatic injection and spray apparatus 10. The drive means 101 is mounted in upper housing 12 on base 105 using mounting blocks 106, 107, 108. The drive means 101 includes a drive cylinder 131, a drive piston 132, a hypodermic needle 191 and disposable syringes 141, 151.

The drive cylinder 131 is movably mounted within mounting block 107 and firmly attached to a carriage 109 using nut bolt 133 and air supply connector 137. The drive cylinder 131 is designed to translate the carriage 109 along a longitudinal axis 102 between an initial resting position adjacent the rear side of mounting block 107 and a fully extended position where nut bolt 133 engages a limit switch 121 on the front side of mounting block 106. The drive piston 132 is movably mounted within drive cylinder 131 and, upon actuation of drive means 101, translates along the longitudinal axis 102 of the drive cylinder 131 toward the hypodermic needle aperture 17 located in the sloped work surface 16 (FIG. 1). A rigid tubular 173, also extending along the longitudinal axis 102, if fixedly attached to a threaded end-portion 171 of the drive piston 132 with a nut 172 and is movably mounted within mounting block 108. The hypodermic needle 191 is fixedly mounted to a threaded surface 176 at the end of rigid tubular 173 using screw clamp 192. The hypodermic needle 191 reciprocates through the hypodermic needle aperture 17 in response to the movement of the rigid tubular 173, which moves in response to the movement by the drive piston 132.

Because it is necessary for the beveled tip 193 of the hypodermic needle 191 to remain at a proper orientation relative to each chick inoculated, the screw clamp 192 securely attaches the hypodermic needle 191 to the rigid tubular 173. The rigid tubular 173 is prevented from rotating by screwing a hexagonal tubular sheath 179 onto the threaded surface 176 of rigid tubular 173 and by shaping the longitudinal surface of guide chamber 181 of mounting block 108 to fit the size and shape of the tubular sheath 179.

In addition, it is necessary to control the distance the hypodermic needle 191 protrudes through the sloped work surface 16 when extended by the drive piston 132. This is accomplished by threading and pressure locking nut bolts 177, 178 along threaded surface 176 of rigid tubular 173 a predetermined distance from mounting block 108. In this manner the drive piston 132 and the rigid tubular 173 translate along the longitudinal axis 102 between an initial resting position where nut 172 engages a threaded end-portion 134 of the drive cylinder 131 and a fully extended position where nut bolts 177, 178 engage mounting block 108.

Retraction cylinders 161, 163 are fixedly mounted to mounting block 107. Correspondingly, retraction pistons 162, 164 are movably mounted within retraction cylinders 161, 163, and are fixedly mounted to the carriage 109 by hex nuts 188, 189. The retraction cylinders 161, 163 are used to assist drive cylinder 131 in returning carriage 109 to its initial resting position adjacent counting block 107.

Injection syringe 141 comprises a plunger 147 slidably mounted within a barrel 142. The barrel 142 in mounted into horizontal slot 145 (FIG. 3) of the carriage 109 so that the barrel rim 143 is retained in vertical slot 144. Locking screw 146 holds the barrel 142 securely in place. Plunger 147 is mounted into slot 149 of mounting block 106 so that plunger head 148 is retained in cavity 115 created between cavity surface 119 of mounting block 106 and cavity surface 117 of dosage block 111. Dosage block 111 is substantially C-shaped and is mounted on the right side of mounting block 106 using screw 113.

A spray syringe 151, comprising a plunger 157 slidably mounted within a barrel 152, is mounted on the side of carriage 109 opposite the injection syringe 141. Locking screw 156 holds the barrel 152 securely in a horizontal slot (not shown) similar to slot 149. The plunger 157 is mounted into vertical slot 159 of mounting block 106 so that plunger head 158 is retained in cavity 116 created between cavity surface 120 of mounting block 106 and cavity surface 118 of dosage block 112. Dosage block 112 is substantially reversed C-shaped and is mounted on the left side of mounting block 106 using a screw (not shown).

Bidirectional flow check valves 201, 236, which direct the flow of vaccine to and away from the syringes 141, 151, and to needle 191 are each securely mounted in recessed grooves 222, 257, located in the base 105 of the upper housing 12, using spring-loaded retention plates 221, 256 respectively. The internal components and the operation of both bidirectional flow check valves 201, 236 are described in more detail below and with reference to FIG. 6.

The injection syringe 141 controls the flow of vaccine from vaccine supply 7 through bidirectional flow check valve 201 and to the hypodermic needle 191. Conduit 194 supplies vaccine from vaccine supply 7 to the bidirectional flow check valve 201 at input connector 197. Conduit 195 connects the barrel 142 of the injection syringe 141 with connector 198 of the bidirectional flow check valve 201. Conduit 196 connects the output connector 199 of the bidirectional flow check valve 201 with the hypodermic needle 191. Conduit 196 enters a cavity 175 located on the smooth surface 174 of rigid tubular 173, extends along the hollowed shaft of rigid tubular 173 and is firmly connected to the hypodermic needle 191 using screw clamp 192.

The spray syringe 151 controls the flow of vaccine from vaccine supply 8 through a bidirectional flow check valve 236 and to the spray apparatus 91. Conduit 229 supplies vaccine from vaccine supply 8 to the bidirectional flow check valve 236 at input connector 232. Conduit 230 connects the barrel 152 of the spray syringe 151 with connector 233 of the bidirectional flow check valve 236. Conduit 231, which extends through spray vaccine aperture 96 on the sloped work surface 16, connects the output connector 234 of the bidirectional flow check valve 236 with spray nozzles **94*a*, 94*b* of the spray apparatus 91**.

Vaccine is injected from the syringes 141, 151 in response to the movement of the carriage 109 from its initial resting position to its fully extended position. Barrels 142, 152, fixedly mounted on the carriage 109, are forced along the shaft of plungers 147, 157 when the plungers 147, 157 are stopped by cavity surfaces 117, 118 respectively. In contrast, vaccine is aspirated into the syringes 141, 151 in response to the movement of the carriage 109 as it returns from its fully extended position to its initial resting position. Barrels 142, 152 are pulled down the shaft of plungers 147, 157 when the plunger heads 148, 158 engage cavity surfaces 119, 120 respectively.

For this reason, the vaccine dosage amounts can be decreased or increased by correspondingly increasing or decreasing the longitudinal distance between cavity surfaces 117 and 119 for injection dosage or between cavity surfaces 118 and 120 for spray dosage. In a preferred embodiment of this invention, dosage blocks 111 or 112 can be exchanged for different dosage blocks having larger or smaller cavities in order to vary the dosage level of each inoculation or spray vaccination.

Figures 6A, 6B:
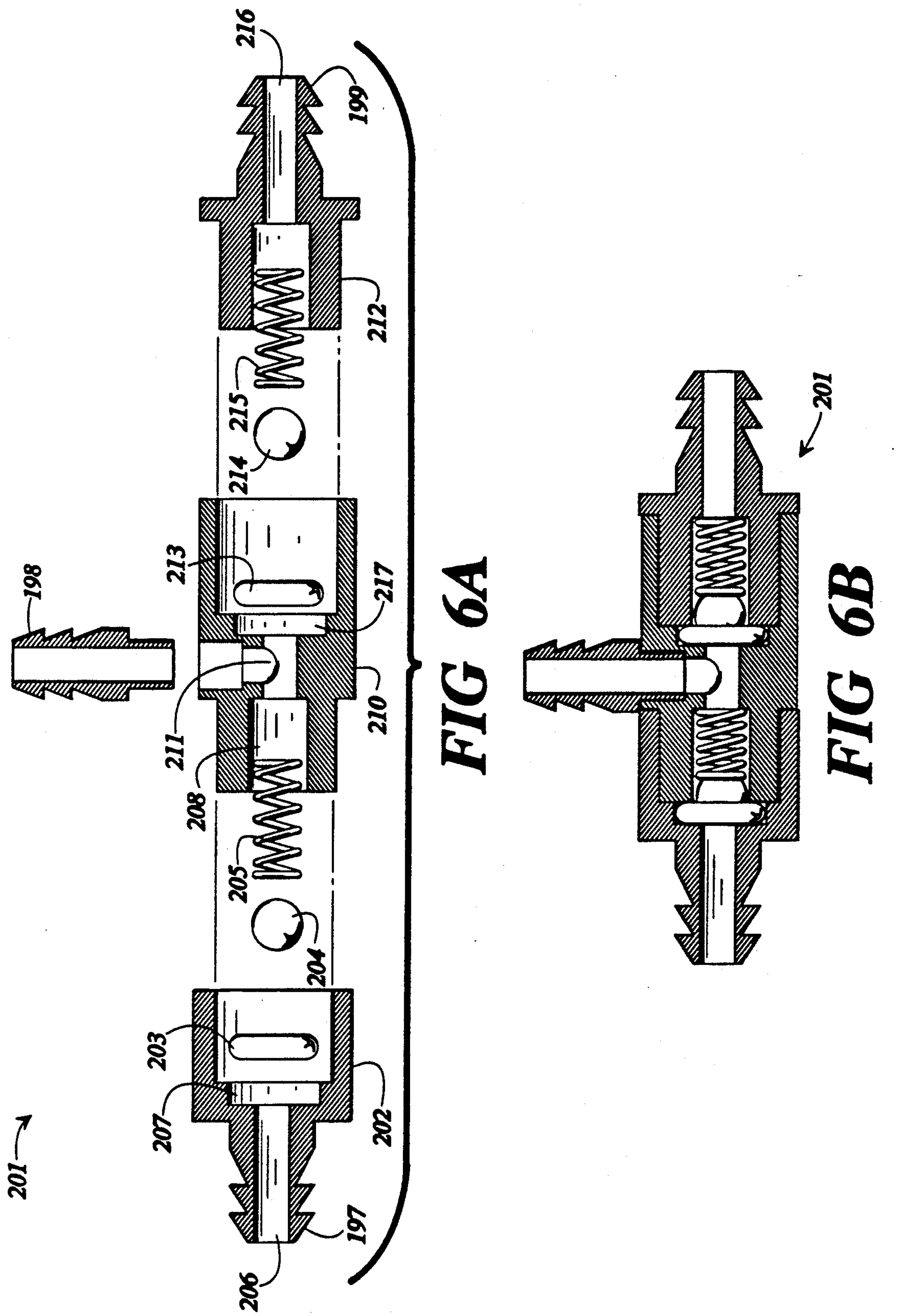
FIG. 6A and 6B are cross-sectional side views of a bidirectional flow check valve, as shown in FIG. 3.

FIGS. 6A and 6B illustrate a cross-sectional view of one of the bidirectional flow check valves. Bidirectional flow check valves 201 and 236 are structurally and functionally identical; however, specific reference is made only to bidirectional flow check valve 201 in communication with the injection syringe 141. The bidirectional flow check valve 201 comprises three main sections: a central chamber 210, an input cap 202 and an output cap 212. The input cap 202 includes the input connector 197, which defines an inlet opening 206. The input cap 202 is slidably mounted onto the central chamber 210 to create an input spring chamber 208 and an output sealing chamber 207, which connect with inlet opening 206. An o-ring 203 is placed in output sealing chamber 207 and a spring 205 is placed in physical communication with a ball 204 in input spring chamber 208. The output cap 212 includes the output connector 199, which defines an outlet opening 216. The output cap 212 is slidably mounted within the central chamber 210 to create an output spring chamber 218 and an input sealing chamber 217, which connect with outlet opening 216. An o-ring 213 is placed in input sealing chamber 217 and a spring 215 is placed in physical communication with a ball 214 in output spring chamber 218. T-chamber 211 is located within central chamber 210 and connects inlet spring chamber 208 and output spring chamber 218 with connector 198, mounted on top of central chamber 210.

When vaccine is aspirated or drawn into the injection syringe 141 (FIGS. 3, 4, 5) through connector 198, both balls 204, 214 are drawn toward T-chamber 211. Ball 204 is pulled away from o-ring 203, which allows vaccine to be drawn through inlet opening 206, output sealing chamber 207, input spring chamber 208, T-chamber 211 and connector 198. Spring 205 prevents ball 204 from sealing the intersection between spring chamber 208 and T-chamber 211. Ball 214, on the other hand, is pulled into sealing contact with o-ring 213; thus, effectively preventing the flow of vaccine through the input sealing chamber 217.

Correspondingly, when vaccine is dispersed or injected from injection syringe 141 (FIGS. 3, 4, 5) through connector 198, both balls 204, 214 are forced away from T-chamber 211. Ball 214 is pushed away from o-ring 213, which allows vaccine to move from connector 198 and through T-chamber 211, input sealing chamber 217, output spring chamber 218 and outlet opening 216. Spring 215 prevents ball 214 from sealing the intersection between spring chamber 218 and outlet opening 216. The ball 204, in this case, is forced into sealing contact with o-ring 203, effectively preventing a backflow of vaccine through output sealing chamber 207.

Figure 7:
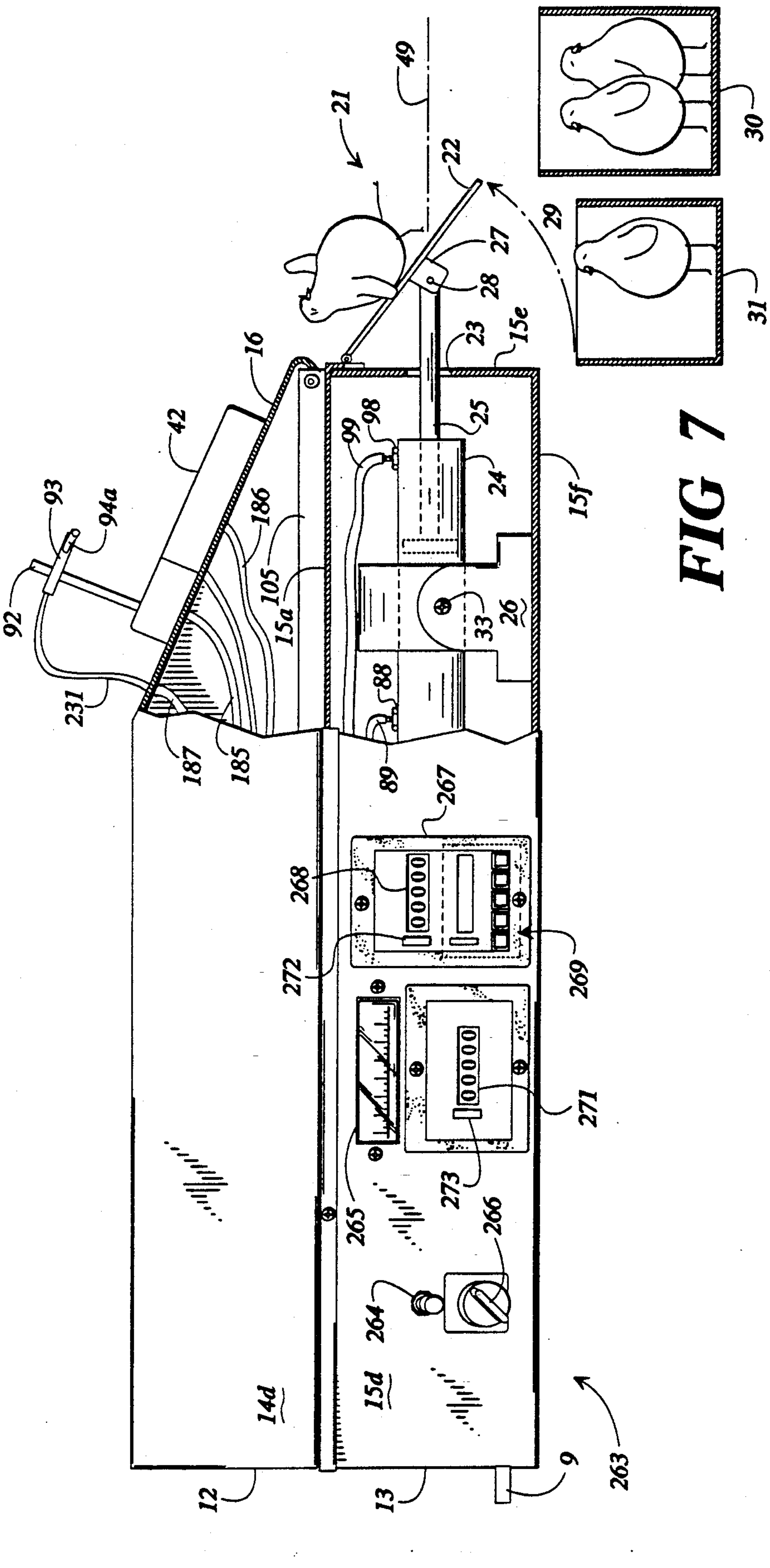
FIG. 7 is a side elevational view of the separation means, the switch means and the spray apparatus of FIG. 1, and a side view of the control panel.

FIG. 7 illustrates a side view of the separation means 21, as described generally in FIG. 1. Separation means 21 comprises a deflector plate 22, a deflection cylinder 24, a deflection piston 25 and two containers 30, 31 for holding vaccinated and unvaccinated chicks, respectively. The deflection cylinder 24 is mounted within a sheath 32, which is pivotally attached with a pin 33 to a clevis 26, mounted onto the bottom panel **15*f* of the lower housing. The deflection piston 25 is movably mounted within the deflection cylinder 24 and is pivotally attached, at its protruding end, with a pin 28 to a clevis 27, mounted onto the back side of the deflector plate 22. The deflection piston 25 translates through a deflector plate aperture 23 and along a longitudinal axis 49 of the deflection cylinder 24 upon actuation of the separation means 21. The deflector plate 22, which is pivotally mounted near the top of the lower housing 13, pivots away from the front panel 15*e*, as shown by direction arrow 29, in response to the movement by the deflection piston 25. In this manner, an inoculated chick sliding down sloped work surface 16 is diverted from falling into container 31 and, instead, falls into container 30**.

SYSTEM OPERATION

Initially the upper housing 12, including the switch means 41 and the spray apparatus 91, is properly mounted on and connected to the lower housing 13. Vaccine from vaccine supplies 7, 8 are connected to the two-way check valves 201, 236 at connectors 197, 232 using conduits 194, 229, respectively. The desired number of chicks per inoculation run is set using counter 269 mounted in counter assembly 267. Run counter 268 and cumulative counter 271 are set to zero using reset buttons 272, 273, respectively.

An external high pressure fluid source, preferably compressed air, is connected to the automatic injection and spray apparatus 10 at air supply input terminal 9. The air pressure into the system is controlled by turning the regulator control knob 264 and reading the pressure on gauge 265. At start up, the drive means 101 and the separation means 21 are at their initial resting positions. The power switch 266 is turned to the "manual" position to cause the apparatus 10 to cycle several times in order to remove any air in the vaccination lines between vaccine supplies 7, 8 and the hypodermic needle 191 and the spray nozzles **94*a*, 94*b*. Once the air has been removed, the power switch 266 is turned to the "auto" position, and the apparatus 10** is ready to begin the inoculation process.

When the power switch 266 is turned to the "auto" position, compressed air flows from the external compressed air source, through input terminal 9 and into the pneumatic logic circuitry 261. Compressed air is directed past an air flow detection sensor 262 (not shown), located in the lower housing 13, and to the upper housing 12 through the connector/socket interchange **36*a*, 37*a*. This compressed air is divided and sent to both switch actuator means 51, 61 through conduits 186, 187, which connect connectors 183, 184 on mounting block 108 to connectors 58, 68 mounted on the bottom surface 43*b* of the switch housing 42, respectively. Compressed air flows continuously through both switch actuator means 51, 61 and greatly reduces the chance of the switch means 41** from becoming clogged with contaminants.

The operator then begins inoculating chicks, one at a time, by placing each chick on the sloped work surface 16 adjacent the switch means 41. The back and head of the chick are placed against the abutment surfaces 45, 46, respectively, using chick retention means 47 as a guide. When both plugs 52, 62 are depressed against the abutment surfaces 45, 46, the sensor 262 detects the stoppage of compressed air flow through conduits 186, 187.

In response to stoppage of compressed air flow, sensor 262, in fluid communication with the pneumatic logic circuitry, actuates the expansion of drive means 101 as follows. Compressed air flows to the upper housing 12 through the connector/socket interchange **36*c*, and then from connector 135 on mounting block 107**, through conduit 139 and into connector 137 on drive cylinder 131. The compressed air initially causes the drive piston 132 and the rigid tubular 173 to extend sufficiently until the hypodermic needle 191 protrudes through the hypodermic needle aperture 17 on sloped work surface 16 and penetrates the chick and bolt 178 engages mounting block 108. Once the drive piston 132 has reached its fully extended position, the continuing buildup of compressed air in the drive cylinder 131 behind the drive piston 132 causes the drive cylinder 131 to translate backwards, toward mounting block 106. Because the carriage 109 is attached to the drive cylinder 131, it too translates toward mounting block 106. Syringes 141, 151, mounted on the carriage 109, also move toward mounting block 106. Syringe plungers 147, 157 correspondingly move with the syringe barrels 142, 152 for a distance equivalent to the width of cavities 115, 116, at which point, plunger heads 148, 158 engage cavity surfaces 117, 118. Plungers 147, 157 are held in place while barrels 142, 152 continue to move along the shafts of the plungers 174, 157 in response to the continuing movement by the carriage 109. Vaccine is thus forced from the syringes 141, 151 to the hypodermic needle 191 and the spray nozzles 94*a*, 94*b*, as described above. The dosage amounts for injection and spraying are independently controlled by the cavity size of dosage blocks 115, 116.

When nut bolt 133 abuts mounting block 106, the flow of vaccine to the chick and the flow of compressed air into connector 137 are stopped and the compression of the drive means 101 is begun when nut bolt 133 at the end of the drive cylinder 131 engages limit switch 121 located on the front side of mounting block 106. The engagement of limit switch 121 allows compressed air supplied to the upper housing 12 through connector/socket interchange 36*g*, and held in conduit 126 between connector 122 and dual-input switch connector 125, mounted on the rear side of mounting block 106, to flow through conduit 127 between connector 123 and dual-input mounting block 106. This compressed air signal travels to the lower housing 13 through connector/socket interchange 36*f*, and is received by the pneumatic logic circuitry, which actuates the compression of the drive means 101. Compressed air then flows to the upper housing 12 through the connector/socket interchange 36*e*, and then from connector 136 on mounting block 107, through conduit 140 and into connector 138 on drive cylinder 131. The compressed air in front of the piston 132 causes the drive piston 132 and the rigid tubular 173 to return to their initial resting positions so that the hypodermic needle 191 is retracted back through the hypodermic needle aperture 17. Compressed air also flows to the upper housing 12 through the connector/socket interchange 36*d*, and then from connectors 165, 166 on mounting block 107, through conduits 169, 170 and into connectors 167, 168 on corresponding retraction cylinders 161, 163. The compressed air entering each retraction cylinder 161, 163 causes the retraction pistons 162, 164, which had been extended with the carriage 109, to retract into the corresponding retraction cylinders 161, 163 until the carriage 109 and the drive cylinder 131 are returned to their original resting positions.

The pneumatic logic circuitry, in response to the closing of limit switch 121, also actuates the separation means 21. Compressed air flows through conduit 89 and into connector 88 on deflection cylinder 24. The compressed air causes the deflection piston 25 to extend through the deflector plate aperture 23 until the deflector plate 22 is extended beyond container 31. The deflector plate 22 remains in an extended position for a sufficient time period to allow the chick to be released by the operator, slide down the sloped work surface 16 and fall into container 30. Compressed air then flows through conduit 99 and into connector 98 on the deflection cylinder 24. The compressed air causes the deflection piston 25 to retract into the deflection cylinder 24 until the deflector plate 22 returns to its resting position adjacent the front panel 15*e* of the lower housing 13. Thus, if a chick were placed on the sloped work surface 16 without actuating the switch means 41, the deflector plate 22 would remain in its resting position and the chick released by the operator would fall into container 31

Each actuation of the switch means 41 causes the run counter 268 and the cumulative counter 271 to increment. When the run counter 268 reaches the same count as the preset value stored by counter 269, the pneumatic logic circuitry disenables the switch means 41, which effectively prevents the apparatus 10 from cycling, and actuates the alarm means 71. Compressed air flows to the upper housing 12 through the connector/socket interchange 36*b*, and then from connector 182 on mounting block 108, through conduit 185 and into connector 78 on the bottom surface 43*b* of the switch housing 42 to actuate the alarm means 71. Exhaust from the alarm means 71 escapes through the exhaust ports 77 and into the upper housing 12 and acts to flush the upper housing 12 of contaminants. The alarm means 71 remains actuated and the switch means 41 remains disenabled until the operator resets the run counter 268.

The container 30 containing the inoculated chicks is then be removed for further processing and an empty, but identical, container 30 is put in its place. The operator begins the next inoculation run using the "missed" chicks, if any, from container 31. This process is continuously repeated throughout the work day. At the end of the day, the total number of chicks inoculated is displayed on the cumulative counter 271.

Cleanup of the apparatus 10 is relatively quick and easy. The syringes 141, 151, the conduits 194, 195, 196, 229, 230, 231 and the hypodermic needle 191 are disconnected and discarded. The upper housing 12 is then removed from the lower housing 13 and are subjected to a liquid wash down. The bidirectional check valves 201, 236 are the only components of the apparatus 10 that must be disinfected.

While this invention has been described in detail with particular reference to a preferred embodiment thereof, it will be understood that variations and modifications can be effected within the scope and spirit of the invention as described hereinbefore and as defined in the appended claims.

We claim:

1. An automatic injection apparatus for injecting vaccine and the like into poultry comprising:

a modular casing construction including a lower housing and an upper housing adapted to mount on said lower housing;

said upper housing including at least one syringe, a hypodermic needle for injecting vaccine into the poultry and a drive means for extending the needle into the poultry and compressing said syringe;

said lower housing containing components for actuating the drive means of said upper housing, so that the upper housing can be removed from the lower housing and one of the housings exchanged with a duplicate housing.

2. The automatic injection apparatus of claim 1 and wherein said upper housing and said lower housing each comprise plugging means for plugging one housing into the other, so that the components for actuating said drive means are in fluid communication with said drive means, and said upper housing is reasonably secured to said lower housing.

3. The automatic injection apparatus of claim 1 and wherein said casing construction further comprises separation means for separating inoculated chicks from chicks placed on said casing construction but not inoculated in response to the actuation of said drive means.

4. The automatic injection apparatus of claim 3 wherein said upper housing includes a sloped work surface on which the chick to be vaccinated is placed, switch means mounted on said sloped work surface responsive to the presence of a chick for actuating said drive means, a hypodermic needle aperture located in said sloped work surface, and wherein said separation means comprises:

a deflector plate pivotally mounted to said casing construction;

a fluid driven cylinder/piston assembly mounted in one of said housings, the piston of said cylinder/piston assembly actuated by said switch means, and said deflector plate responsive to the movement of said piston, so that when said automatic injection apparatus cycles, the chick that is inoculated slides down said sloped work surface is deflected by said deflector plate and falls into a container for vaccinated chicks.

5. An automatic injection apparatus for injecting vaccine and the like into chicks including a housing defining a hypodermic needle aperture, said housing containing at least one syringe and a hypodermic needle in fluid communication with said syringe, drive means for reciprocating said needle from within said housing through the aperture to penetrate chicks outside said housing and for injecting vaccine from the syringe through said needle into the chicks, and switch means mounted on said housing for actuating said drive means, said switch means comprising:

a switch housing including first and second abutment surfaces facing said aperture and located at different positions about said aperture; and first and second moveable switch actuator means mounted in said switch housing and protruding from said abutment surfaces, said switch means adapted to actuate said drive means when both said first and second switch actuator means are simultaneously moved by a chick which has been placed by an operator into engagement with both abutment surfaces, whereby when both said movable switch actuator means are simultaneously moved by the chick, said drive means is actuated and the chick is inoculated.

6. The automatic injection apparatus of claim 5 and wherein said abutment surfaces of said switch housing are located substantially at right angles relative to each other and to the mounting surface of said housing.

7. The automatic injection apparatus of claim 6 and wherein said switch housing further includes chick retention means formed in a shape which corresponds to the shape of the head and upper back portion of a typical chick for guiding a chick to a position aligned with said aperture and said switch means during vaccination.

8. The automatic injection apparatus of claim 7 and wherein said chick retention means comprises a chick head retaining surface extending from said second abutment surface of the switch housing and adjacent said second moveable switch actuator means so that the head of a chick is guided toward the second movable switch actuator means during vaccination.

9. The automatic injection apparatus of claim 5 and wherein said switch means further comprises:

a compressed air source;

said first and second abutment surfaces each defining an outlet opening in communication with said compressed air source and through which compressed air flows;

said first and second switch actuator means each having:

a plug mounted for movement toward and away from said outlet opening between an open position wherein the compressed air flows freely through the outlet opening and about said plug and a closed position wherein the compressed air is blocked from escaping the outlet opening and about said plug; and sensing means for detecting the stoppage of compressed air flow through both outlet openings and for actuating said drive means.

10. The automatic injection apparatus of claim 9 and wherein said switch actuator means further comprises purging means for preventing said switch actuator means from becoming clogged by feathers, dirt and the like during operation of said apparatus.

11. The automatic injection apparatus of claim 10 and wherein said purging means is the compressed air flow through said outlet openings and about said plugs which prevents feathers, dirt and the like from clogging said switch actuator means during operation of said apparatus.

12. The automatic injection apparatus of claim 5 further including a compressed air source, a counter in fluid communication with said compressed air source and adapted to count each inoculation and provide a compressed air signal upon completion of a predetermined number of counts, and wherein said switch means further comprises:

alarm means mounted within said switch housing and responsive to said compressed air signal for generating an alarm detectable by the operator for notifying the operator of the completion of a predetermined number of inoculations; and exhaust means for directing the compressed air from said alarm means into said housing so that the housing is flushed by the air of feathers, dirt and the like.

13. The automatic injection apparatus of claim 5 and wherein said housing further comprises a spray apparatus mounted on said switch housing, said spray apparatus in fluid communication with at least one syringe within said housing and actuated by said drive means.

14. The automatic injection apparatus of claim 5 and wherein said housing further comprises separation means for separating inoculated chicks from chicks placed on said housing but not inoculated in response to the actuation of said drive means.

15. The automatic injection apparatus of claim 14 wherein said housing includes a sloped work surface on which the chick to be vaccinated is placed, said aperture located in the sloped work surface, and wherein said separation means comprises:

a deflector plate pivotally mounted to said housing below said work surface;

a fluid driven cylinder/piston assembly mounted in said housing, the piston of said cylinder/piston assembly actuated by said switch means, and said deflector plate responsive to the movement of said piston, so that when said automatic injection apparatus cycles, the chick that is inoculated slides down said sloped work surface is deflected by said deflector plate and falls into a container for vaccinated chicks.

16. The automatic injection apparatus of claim 5 wherein said housing includes a sloped work surface on which the chick to be vaccinated is placed, said aperture located in the work surface, said first abutment surface of said switch housing is located on said work surface adjacent the aperture and parallel to the slope of said work surface and said second abutment surface of said switch housing is located above the aperture on said work surface and perpendicular to the slope of said work surface such that said aperture is surrounded on two sides by said switch housing.

17. An automatic injection apparatus for injecting vaccine and the like into chicks including a housing defining a hypodermic needle aperture and including at least one syringe in fluid communication with a vaccine supply and a hypodermic needle in fluid communication with said syringe, drive means for reciprocating said needle from within said housing through the aperture to penetrate chicks outside said housing, for injecting vaccine from said syringe through said needle into the chick and for aspirating vaccine from said vaccine supply into said syringe, said drive means comprising:

a fluid driven cylinder/piston assembly with a cylinder movably mounted in said housing and a piston movably mounted in said cylinder, said needle responsive to the movement of said piston to extend through the aperture of said housing, and said syringe responsive to the movement of said cylinder to dispense vaccine to said needle, so that when a chick is positioned adjacent the aperture and the cylinder/piston assembly is expanded, the needle is extended through the aperture and penetrates the chick and vaccine is dispensed through the needle to the chick wherein said housing includes a sloped work surface on which the chick to be vaccinated is placed, said aperture located in the work surface, a switch means mounted on said housing for actuating said drive means, said switch means comprising:

a switch housing including first and second abutment surfaces facing said aperture; and first and second moveable switch actuator means mounted in said switch housing and protruding from said abutment surfaces, said switch means adapted to actuate said drive means when both said first and second actuator means are simultaneously moved by a chick which has been placed by an operator into engagement with both abutment surfaces, whereby when both said movable switch actuator means are simultaneously moved by the chick, said drive means is activated, and the chick is inoculated.

18. The automatic injection apparatus of claim 17 and wherein said drive means further comprising:

a fluid driven cylinder/piston assembly with a cylinder movably mounted in said housing and a piston movably mounted in said cylinder, said needle responsive to the movement of said piston to retract through the aperture of said housing, and said syringe responsive to the movement of said cylinder to aspirate vaccine from said vaccine supply and into said syringe, so that after a chick has been vaccinated, the needle is retracted into said housing and said syringe is refilled with vaccine and ready for the next vaccination.

19. The automatic injection apparatus of claim 17 and wherein said switch means further comprises:

a compressed air source;

said first and second abutment surfaces each defining an outlet opening in communication with said compressed air source and through which compressed air flows;

said first and second switch actuator means each having:

a plug mounted for movement toward and away from said outlet opening between an open position wherein the compressed air flows freely through the outlet opening and about said plug and a closed position wherein the compressed air is blocked from escaping the outlet opening and about said plug; and sensing means for detecting the stoppage of compressed air flow through both outlet openings and for actuating said drive means.

20. The automatic injection apparatus of claim 19 and wherein said switch actuator means further comprises purging means for preventing said switch actuator means from becoming clogged by feathers, dirt and the like during operation of said apparatus.

21. The automatic injection apparatus of claim 20 and wherein said purging means is the compressed air flow through said outlet openings and about said plugs which prevents feathers, dirt and the like from clogging said switch actuator means during operation of said apparatus.

22. The automatic injection apparatus of claim 17 further including a compressed air source, a counter in fluid communication with said compressed air source and adapted to count each inoculation and provide a compressed air signal upon completion of a predetermined number of counts, and wherein said switch means further comprises:

alarm means mounted within said switch housing and responsive to said compressed air signal for generating an alarm detectable by the operator for notifying the operator of the completion of a predetermined number of inoculations; and exhaust means for directing the compressed air from said alarm means into said housing so that the housing is flushed by the air of feathers, dirt and the like.

23. The automatic injection apparatus of claim 17 and wherein said housing further comprises a spray apparatus mounted on said switch housing, said spray apparatus in fluid communication with at least one syringe within said housing and actuated by said drive means.

24. The automatic injection apparatus of claim 17 and wherein said housing further comprises separation means for separating the inoculated chicks from chicks placed on said housing but not inoculated in response to the actuation of said drive means.

25. The automatic injection apparatus of claim 24 and wherein said housing includes a sloped work surface on which the chick to be vaccinated is placed, said aperture located within the sloped work surface, and wherein said separation means comprises:

a deflector plate pivotally mounted to said housing below said work surface;

a fluid driven cylinder/piston assembly mounted in said housing, the piston of said cylinder/piston assembly actuated by said switch means, and said deflector plate responsive to the movement of said piston, so that when said automatic injection apparatus cycles, the chick that is inoculated slides down said sloped work slope, is deflected by said deflector plate and falls into a container for vaccinated chicks.

26. An automatic injection apparatus for injecting vaccine and the like into chicks comprising:

a housing defining a hypodermic needle aperture, said housing containing at least one syringe and a hypodermic needle in fluid communication with said syringe, and drive means for reciprocating said needle to move said needle from within said housing through the aperture to penetrate chicks outside said housing and for injecting vaccine from the syringe through said needle into the chicks;

switch means mounted on said housing for actuating said drive means; and purging means for passing compressed air through said switch means before and after each injection which prevents said switch means from becoming clogged by feathers, dirt and the like during operation of the apparatus.

27. An automatic injection apparatus for injecting vaccine and the like into chicks comprising:

a housing defining a hypodermic needle aperture, said housing containing at least one syringe and a hypodermic needle in fluid communication with said syringe, and drive means for reciprocating said needle to move said needle from within said housing through the aperture to penetrate chicks outside said housing and for injecting vaccine from the syringe through said needle into the chicks;

switch means mounted on said housing for actuating said drive means;

a compressed air source;

a counter in fluid communication with said compressed air source and adapted to count each inoculation and provide a compressed air signal upon completion of a predetermined number of counts, said switch means including a housing, and alarm means mounted within said switch housing and responsive to said compressed air signal for generating an alarm detectable by the operator for notifying the operator of the completion of a predetermined number of inoculations; and exhaust means for directing the compressed air from said alarm means into said switch housing so that the housing is flushed by the air of feathers, dirt and the like.

28. An automatic injection apparatus for injecting vaccine and the like into chicks including a housing defining a hypodermic needle aperture and including first and second syringes in communication with first and second vaccine supplies, a hypodermic needle in fluid communication with said first syringe, a spray apparatus mounted on said housing and in fluid communication with said second syringe, and drive means for reciprocating said needle to move said needle from within said housing through the aperture to penetrate chicks outside said housing, for injecting vaccine from said first syringe through the needle into the chicks, for spraying vaccine from said second syringe through the spray apparatus onto the chicks and for aspirating vaccine from said first and second vaccine supplies into said first and second syringes, said drive means comprising:

a fluid driven cylinder/piston assembly with a cylinder movably mounted in said housing and a piston movably mounted in said cylinder, said needle responsive to the movement of said piston to extend through the aperture of said housing, and both of said first and second syringes actuated by the movement of said cylinder to dispense vaccine to said needle and to said spray apparatus, so that when a chick is positioned adjacent the aperture and the cylinder/piston assembly is expanded, the needle is extended through the aperture and penetrates the chick and vaccine is dispensed to the chick through both the needle and the spray apparatus.

29. An automatic injection apparatus for injecting vaccine and the like into chicks comprising:

a housing defining a hypodermic needle aperture, said housing containing at least one syringe and a hypodermic needle in fluid communication with said syringe, and drive means for reciprocating said needle to move said needle from within said housing through the aperture to penetrate chicks outside said housing and for injecting vaccine from the syringe through said needle into the chicks;

switch means mounted on said housing for actuating said drive means;

separation means for separating inoculated chicks from chicks placed on said housing but not inoculated in response to the actuation of said drive means.

30. The automatic injection apparatus of claim 29 wherein said upper housing includes a sloped work surface on which the chick to be vaccinated is placed, switch means mounted on said sloped work surface responsive to the presence of a chick for actuating said drive means, a hypodermic needle aperture located in said sloped work surface and wherein said separation means comprises:

a deflector plate pivotally mounted to said casing construction;

a fluid driven cylinder/piston assembly mounted in one of said housings, the piston of said cylinder/-piston assembly actuated by said switch means, and said deflector plate responsive to the movement of said piston, so that when said automatic injection apparatus cycles, the chick that is inoculated slides down said sloped work surface is deflected by said deflector plate and falls into a container for vaccinated chicks.

* * * * *